United States Patent
Dougherty, Jr. et al.

(10) Patent No.: US 8,870,843 B2
(45) Date of Patent: Oct. 28, 2014

(54) DISPOSABLE ABSORBENT PRODUCT WITH TEMPORARY ADHESIVE ATTACHMENT AND RELATED METHODS

(75) Inventors: Eugene Patrick Dougherty, Jr., Newark, DE (US); Raymond Martin Carter, Philadelphia, PA (US)

(73) Assignee: SCA Hygiene Products AB, Gothenburg (SE)

( * ) Notice: Subject to any disclaimer, the term of this patent is extended or adjusted under 35 U.S.C. 154(b) by 213 days.

(21) Appl. No.: 13/568,952

(22) Filed: Aug. 7, 2012

(65) Prior Publication Data

US 2014/0046284 A1 Feb. 13, 2014

(51) Int. Cl.
*A61F 13/15* (2006.01)

(52) U.S. Cl.
USPC ............................ 604/389; 604/391; 604/392

(58) Field of Classification Search
CPC ............ A61F 13/5622; A61F 13/5633; A61F 13/5644; A61F 13/581; A61F 13/586; A61F 13/622; A61F 13/64; A61F 13/82
USPC .......................................... 604/389, 391, 392
See application file for complete search history.

(56) References Cited

U.S. PATENT DOCUMENTS

| | | | | |
|---|---|---|---|---|
| 4,869,724 | A * | 9/1989 | Scripps | 604/389 |
| 5,832,535 | A | 11/1998 | Davis | |
| 6,135,988 | A * | 10/2000 | Turner et al. | 604/387 |
| 6,177,482 | B1 | 1/2001 | Cinelli et al. | |
| 6,258,076 | B1 | 7/2001 | Glaug et al. | |
| 6,277,106 | B1 * | 8/2001 | Boudry et al. | 604/394 |
| 6,491,677 | B1 * | 12/2002 | Glaug et al. | 604/387 |
| 6,632,210 | B1 | 10/2003 | Glasgow et al. | |
| 6,645,188 | B2 * | 11/2003 | Kusibojoska et al. | 604/385.11 |
| 6,918,900 | B2 * | 7/2005 | Johnson | 604/385.03 |
| 7,156,834 | B2 * | 1/2007 | Kawata et al. | 604/392 |
| 2002/0095130 | A1 * | 7/2002 | Seitter et al. | 604/389 |

(Continued)

FOREIGN PATENT DOCUMENTS

| | | |
|---|---|---|
| EP | 0 873 739 A1 | 10/1998 |
| WO | 98/27910 A1 | 7/1998 |
| WO | 00/72791 A1 | 12/2000 |
| WO | 03/017904 A1 | 3/2003 |

OTHER PUBLICATIONS

Notification of Transmittal of International Search Report (Form PCT/ISA/210) and the Written Opinion of the International Searching Authority (Form PCT/ISA/237) issued on Sep. 19, 2013, by the European Patent Office in corresponding International Application No. PCT/EP2013/065811. (10 pages).

*Primary Examiner* — Lynne Anderson (74) *Attorney, Agent, or Firm* — Buchanan Ingersoll & Rooney PC (57) ABSTRACT

A disposable absorbent product extends longitudinally along a longitudinal axis and laterally along a transverse axis, with the transverse axis conceptually dividing the product into first and second hemispheres. The product has a permeable topsheet, an impermeable backsheet overlaying the topsheet, and an absorbent core disposed between the topsheet and the backsheet for storing fluid secreted by the wearer of the disposable absorbent product. Each of a pair of side regions extends laterally outboard of the absorbent core, with each side region having a first face configured to face the wearer during use and a second face opposite the first face. The product also has at least one skin-friendly adhesive element in the first hemisphere in at least one of the side regions for temporarily attaching the disposable absorbent product to the skin of the wearer.

26 Claims, 4 Drawing Sheets

(56) References Cited

U.S. PATENT DOCUMENTS

2004/0096489 A1 5/2004 Fabo
2008/0134418 A1 6/2008 Johansson et al.
2008/0262461 A1 10/2008 de Dier et al.

* cited by examiner

DISPOSABLE ABSORBENT PRODUCT WITH TEMPORARY ADHESIVE ATTACHMENT AND RELATED METHODS

TECHNICAL FIELD

The present invention is generally related to absorbent products and, more particularly, to disposable absorbent products that are worn by humans for the containment and absorption of fluid bodily secretions.

BACKGROUND

Disposable absorbent products for absorption of bodily fluids are available in different types, designs, and dimensions. For example, training pants, baby diapers, adult diapers, and incontinence guards are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

Disposable absorbent products such as adult diapers (briefs) are often worn by people with limited mobility, such as the elderly. Dexterity on the part of the wearer or on the part of the caregiver is often required to properly apply the diaper onto the body of the wearer. And this dexterity is especially required when a diaper is applied onto a standing person, because application requires supporting the weight of the diaper while centering and maneuvering same and while trying to fasten the diaper together, on the body of the wearer. Application of a diaper to a standing child or adult may typically therefore be a challenging and stressful experience for the person wearing the diaper, as well as to caregivers. In the case of older, incontinent adults in a nursing home, for example, application of an adult diaper may require the effort and coordination of two or more caregivers, or even the use of a lifting device, all of which is detrimental to the operation of the nursing home.

Similarly, application of a diaper or similar product to a person that is lying down may also be a challenging and stressful experience. More specifically, a mother changing her baby's diaper seeks to orient and center the front and back parts of the diaper on her baby's child prior to fastening the diaper together. For example a mother may first orient and center the back part of the diaper and then proceed to orient and center the front part of the diaper. Often, however, the squirming motion of the baby results in the back part of the diaper moving or reorienting to an undesired position prior to fastening, which results in an improperly fit diaper. This improper fitting of the diaper may result in leakage of urine and/or general discomfort to the baby.

Accordingly, it is desirable to provide disposable absorbent products that address these and other shortcomings of conventional disposable absorbent products. More specifically, it is desirable to provide disposable absorbent products such as diapers and the like that make the application thereof onto a wearer's body a less challenging and less stressful experience.

SUMMARY

In one embodiment, a disposable absorbent product is provided extending longitudinally along a longitudinal axis and laterally along a transverse axis, with the transverse axis conceptually dividing the product into first and second hemispheres. The product has a topsheet, a backsheet overlaying the topsheet, and an absorbent core disposed between the topsheet and the backsheet for storing fluid secreted by the wearer of the disposable absorbent product. Each of a pair of side regions extends laterally outboard of the absorbent core, with each side region having a first face configured to face the wearer during use and a second face opposite the first face.

The product also has at least one skin-friendly adhesive element in the first hemisphere or in the second hemisphere, in at least one of the side regions, for temporarily attaching the disposable absorbent product to the skin of the wearer. A fastening component in the first hemisphere is configured for securing the first and second hemispheres to one another on the wearer. The at least one skin-friendly adhesive element is in contact with the second hemisphere when the first and second hemispheres are secured to one another on the wearer.

The fastening component in a specific embodiment includes the hook or loop member of a hook-and-loop fastener. Additionally or alternatively, the fastening component may be located on the first face of one of the side regions. The fastening component may include a tab extending outwardly from one of the side regions. In a specific embodiment, the at least one skin-friendly adhesive element includes first and second skin-friendly adhesive elements that are located on respective ones of the pair of side regions. Additionally, the first and second skin-friendly adhesive elements may be substantially equidistant from the longitudinal axis of the product. The at least one skin-friendly adhesive element may include first and second spaced apart skin-friendly adhesive elements that are located on one of the side regions.

The first and second skin-friendly adhesive elements may be longitudinally spaced from one another. In a specific embodiment, the at least one skin-friendly adhesive element is located on the first face of one of the side regions. The at least one skin-friendly adhesive element may have a tackiness value in the range of about 0.1 inches to about 2 inches. In another specific embodiment, the at least one skin-friendly adhesive element has an adhesive strength, when adhered to skin, in the range from about 0.5N to about 5N, as measured by the Standard Test Method for Tack of Pressure-Sensitive Adhesives by Rolling Ball using a 1 mil polyester film. Additionally or alternatively, the at least one skin-friendly adhesive element may be free from tackifiers and biocides. In other embodiments, the at least one skin-friendly adhesive element is made up of an adhesive having a pH value of about 5 or less.

The at least one skin-friendly adhesive element may be made up of an adhesive having a softness less than about 10 mm. The side regions, in some embodiments, define respective belt portions of the product configured to wrap around the body of the wearer. The product may have a front portion configured to face the front part of the wearer's body, a back portion configured to face the back part of the wearer's body, and a crotch portion between the front and back portions, with the back portion being located in the first hemisphere of the product.

In another embodiment, a disposable absorbent diaper is provided that extends longitudinally along a longitudinal axis and laterally along a transverse axis. The diaper also has a front portion configured to face the front of the wearer's body during use, and a back portion configured to face the back of the wearer's body during use. The product has a permeable topsheet, as well as an impermeable backsheet overlaying the topsheet. An absorbent core is disposed between the topsheet and the backsheet for storing fluid secreted by the wearer of the diaper. Each of a pair of side panels in the back portion extends laterally outboard of the absorbent core, with each of those side panels having a first face configured to face the wearer during use and a second face opposite the first face. The diaper also has a skin-friendly adhesive element in the back portion, on the first face of each of the side panels, for temporarily attaching the diaper to the skin of the wearer.

At least one hook-and-loop fastener member is present in the back portion and is configured for securing the front and back portions to one another on the wearer. The skin-friendly adhesive element on the first face of each of the side panels is in contact with the front portion when the front and back portions are secured to one another by the at least one hook-and-loop fastener member. The at least one hook-and-loop fastener member may include first and second hook-and-loop fastener members located on the side panels. Additionally or alternatively, the at least one hook-and-loop fastener member is a hook fastener that is configured for direct entangled engagement with the backsheet in the front portion. In a specific embodiment, the diaper also has at least one loop fastener member in the front portion, with the at least one hook-and-loop fastener member being a hook fastener that is configured for entangled engagement with the at least one loop fastener member in the front portion.

In yet another embodiment, a belted disposable absorbent product is provided that extends longitudinally along a longitudinal axis and laterally along a transverse axis, with the product further having a front portion configured to face the front of the wearer's body during use and a back portion configured to face the back of the wearer's body during use. The product has a permeable topsheet, and an impermeable backsheet overlaying the topsheet. An absorbent core is disposed between the topsheet and the backsheet for storing fluid secreted by the wearer of the disposable absorbent product. The product further has a pair of belt portions in the back portion of the product extending laterally outboard of the absorbent core. Each of the belt portions has a first face configured to face the wearer during use and a second face opposite the first face.

A skin-friendly adhesive element in each of the belt portions temporarily attaches the disposable absorbent product to the skin of the wearer. Each of a pair of hook-and-loop fastener members in the back portion is configured for securing the front and back portions of the product to one another on the wearer. Each of the skin-friendly adhesive elements is in contact with the front portion of the product when the front and back portions are secured to one another by the hook-and-loop fastener members. The hook-and-loop fastener members may be located on the belt portions.

Additionally or alternatively, the skin-friendly adhesive elements are located on the respective first faces of said belt portions. The hook-and-loop fastener members in specific embodiments are hook fasteners that are configured for direct entangled engagement with the backsheet in the front portion. In a specific embodiment, the skin-friendly adhesive elements and the hook-and-loop fastener members are located on the first faces of the belt portions. The product may additionally have at least one loop fastener member in the front portion, with at least one of the hook-and-loop fastener members being a hook fastener that is configured for entangled engagement with the at least one loop fastener member in the front portion.

BRIEF DESCRIPTION OF THE DRAWINGS

The objectives and features of the invention will become more readily apparent from the following detailed description taken in conjunction with the accompanying drawings in which.

DETAILED DESCRIPTION

To the extent that any meaning or definition of a term in this written document conflicts with any meaning or definition of the term in a document incorporated by reference, the meaning or definition assigned to the term in this written document shall govern. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
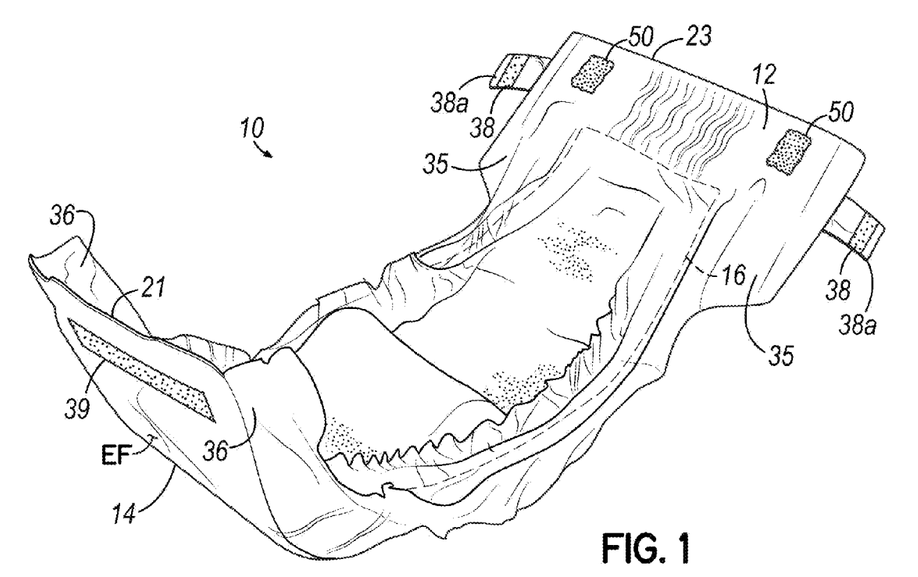
FIG. 1 is a perspective view of a disposable absorbent product in accordance with one embodiment of the invention.
Figure 2:
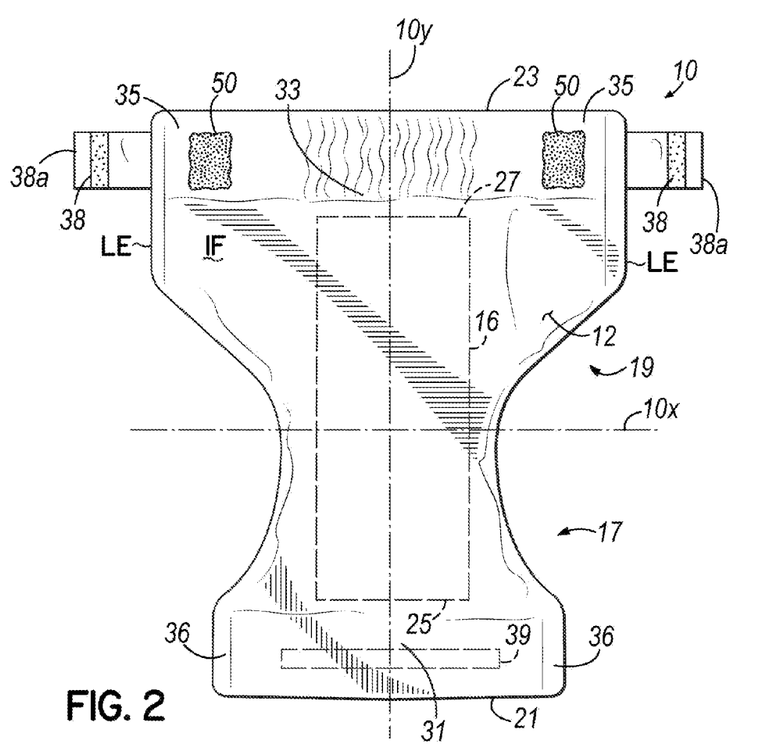
FIG. 2 is a top view of the exemplary product of FIG. 1.

With reference to the figures, and more particularly to FIGS. 1 and 2, an exemplary disposable absorbent product in the form of a diaper 10 is illustrated. For ease of understanding, some of the features of diaper 10 shown in FIG. 1 are obviated from FIG. 2. Diaper 10 could be a baby diaper or an adult diaper ("brief"), for example. Diaper 10 extends in the longitudinal direction along a longitudinal axis $10y$, and extends laterally along a transverse axis $10x$ orthogonal to the longitudinal axis $10y$, as illustrated in FIG. 2. Diaper 10 has a topsheet 12 and a backsheet 14 disposed opposite the topsheet 12, such that the topsheet 12 and backsheet 14 are in an overlaying relationship with one another. An absorbent core 16 is disposed between the topsheet 12 and backsheet 14, as more fully explained below. In use, the topsheet 12 at least partially defines an interior face IF of the diaper 10 that faces the body of the wearer, in use. The backsheet 14, in contrast, faces away from the body of the wearer, in use, and accordingly at least partially defines an exterior face EF of the diaper 10.

The topsheet 12 is at least partially made of a permeable, hydrophilic material such as a hydrophilic nonwoven, and may be in the form of a single, continuous layer spanning across the length and/or width of the diaper 10, or may alternatively be in the form of two or more layers of the same material or of materials different from one another that jointly, rather than individually, span the length and/or width of the diaper 10. In that regard, and as more fully explained below, the term "topsheet" as used herein can refer to a single layer that lies over the absorbent core 16 as well as partially or entirely over regions laterally outboard of the core 16, or can alternatively refer to a plurality of layers of material joined to one another so as to span the entire width of diaper 10.

The backsheet 14 is at least partially made of an impermeable, hydrophobic material, such as a hydrophobic nonwoven or a laminate made of one or more layers of nonwoven material and one or more layers of polypropylene or polyethylene film. Backsheet 14 may be in the form of a single, continuous layer spanning across the length and/or width of the diaper 10, or may alternatively be in the form of two or more layers of the same material or of materials different from one another that jointly, rather than individually, span the length and/or width of the diaper 10.

The pad 10 also includes, as discussed above, an absorbent core 16, disposed between the topsheet 12 and backsheet 14. The core 16 is configured to absorb and retain body fluids, such as urine, blood, and/or menses, secreted by the wearer. The core 16 is made up of fluff pulp or a combination of fluff pulp or some other natural or synthetic fluid management material, and a fluid storage material such as superabsorbent material ("SAP") or some other natural or synthetic fluid storage material. While not shown, core 16 may also include an optional acquisition material layer or another type of layer (e.g., an airlaid material layer) adjacent the topsheet 12, which is primarily configured to distribute and/or direct fluids received through the topsheet 12 onto other portions of core 16 that are primarily configured to store fluids secreted by the wearer. The core 16 could be generally rectangular, or have an hourglass shape, or have any other regular or irregular, symmetrical or asymmetrical shape.

With continued reference to FIGS. 1-2, the transverse axis 10x conceptually divides the diaper 10 into front and back longitudinal hemispheres 17, 19. The diaper 10 thus extends longitudinally between a front longitudinal end 21 and a back longitudinal end 23. The core 16, in turn, extends longitudinally between a front edge 25 and a back edge 27. While the front and back edges 25, 27 are illustrated in the figures as generally rectilinear, it is understood either or both may have any other regular or irregular shape, such as one including curves, straight line segments or any other shape. The front longitudinal end 21 and the front edge 25 fall generally within the front portion of the diaper 10 which, in use, generally faces the front part of the body of the wearer. In contrast, the back longitudinal end 23 and the back edge 27 fall generally within the back portion of the diaper 10, which generally faces the back part of the body of the wearer. In this regard, and as used herein, the terms "front portion" and "back portion," when used to describe parts of the diaper 10, do not imply the existence of any specific structural boundaries within the diaper 10, but instead refer to the general areas that, in use, lie respectively against the front and back parts of the body of the wearer. In that regard, the diaper 10 is also considered to include a crotch portion located between the front and back portions thereof, which is a region of diaper 10 that generally lies against the crotch of the wearer, in use.

The core 16 of the illustrated embodiment is positioned relative to other portions of the diaper 10, such that a front end portion 31 is defined between the front longitudinal end 21 and the front edge 25 of the core 16. The exemplary core 16 is also positioned so as to define a back end portion 33 between the back longitudinal end 23 and the back edge 27 of the core 16. Those of ordinary skill in the art will readily appreciate, however, that other relative positions of the core 16 are possible which may, for example, define only one end portion 31, 33 or define no such end portions at all. In other words, alternative configurations are contemplated in which the core 16 may instead extend to one or both of the longitudinal ends 21, 23.

With continued reference to FIGS. 1-2, diaper 10 includes a pair of side regions in the form, in this embodiment, of side panels 35, laterally outboard of the core 16 in the back portion of the diaper 10. The side panels 35 are thus made up of portions of the topsheet 12 and backsheet 14 that are joined together with adhesive elements, and/or or mechanically (e.g., CPW or ultrasonic bonding), for example, so as to form an integral structure. In specific embodiments, the side panels 35 may include elastomeric portions (not shown) that allow the side panels 35 to laterally stretch with relative ease, to accommodate convenient application of diaper 10 and provide comfort to the wearer. The elastomeric portions may in some embodiments extend into areas directly beneath the core 16. Diaper 10 similarly has another pair of side regions 36, also laterally outboard of core 16, but located generally in the front portion of the diaper 10. The construction of the side regions 36 is generally similar to that of the side panels 35, which may for example optionally include elastomeric portions (not shown) similar to or different from the optional elastomeric portions in side panels 35.

Diaper 10 has a pair of fastening components such as mechanical fasteners or adhesive or cohesive tapes, generally assigned the numeral 38, located in the back portion of diaper 10. In the illustrated embodiment, the fastening components 38 are supported on respective tabs 38a extending generally from the lateral ends LE of the diaper 10. Other embodiments are also contemplated within the scope of the present disclosure, in which the fastening components 38 are supported directly on the side panels 35, rather than on tabs, and located generally adjacent the lateral ends LE of diaper 10.

The fastening components 38 are engageable with a cooperating fastening component or feature 39 on the front portion of the diaper 10 to secure the diaper 10 in place, on the body of the wearer. The cooperating fastening feature 39 may for example be in the form of an adhesive or cohesive landing zone or patch, or a mechanical fastener landing zone or patch (e.g., containing hooks or loops) coupled (e.g., mechanically and/or adhesively attached) to the backsheet 14 and which cooperates with fastening components 38 to secure the diaper 10 in place, on the body of the wearer. In the exemplary embodiment of FIGS. 1 and 2, the fastening components 38 include hook members and the cooperating fastening feature 39 includes a loop member. Entangled engagement of the hook and loop members with one another secures the front and back portions of diaper 10 to one another on the body of the wearer. Other embodiments are similarly contemplated in which the fastening components 38 are loop members that are engageable with a hook-type fastening feature 39. Yet other embodiments are contemplated in which fastening feature 39 includes two or more hook fasteners or loop fasteners, rather than a single structure (e.g., the exemplary single structure making up fastening feature 39 in FIGS. 1-2).

Fastening feature 39 may alternatively be defined by the exterior surface of the backsheet 14, so long as that surface is configured to directly entangle the fastening component 38 sufficiently so as to secure the diaper 10 in place i.e., on the body of the wearer. While the embodiment of FIGS. 1-2 has the fastening components 38 located in the back portion of diaper 10 and the cooperating fastening feature 39 being located in the front portion, embodiments are contemplated in which the fastening components 38 are instead located in the front portion of diaper 10, while the cooperating fastening feature 39 is located in the back portion of diaper 10, so long as they are positioned so as to engage one another to secure the diaper 10 in place on the body of the wearer.

Figure 3:
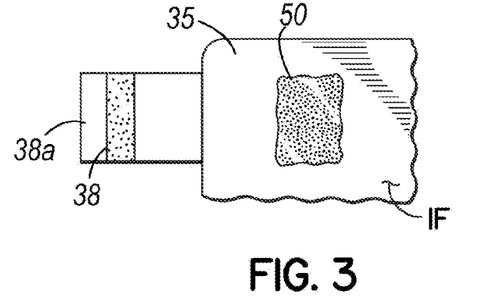
FIG. 3 is an enlarged, broken-away view of a portion of the product of FIGS. 1 and 2.
Figure 4:
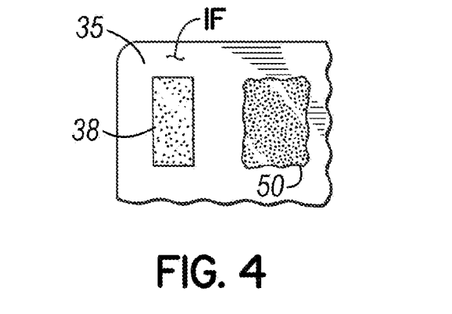
FIG. 4 is an enlarged, broken-away view of a side panel of an exemplary disposable absorbent product in accordance with another embodiment of the invention.

With continued reference to FIGS. 1-2, and further referring to FIGS. 3 and 4, diaper 10 has at least one additional fastening element 50 used for temporary attachment to the skin of the wearer. More specifically, in the illustrated embodiment, diaper 10 has two such additional fastening elements 50. Each fastening element 50 is a skin-friendly adhesive element that has a relatively low level of adhesion to human skin, so as to permit temporary attachment of the unloaded diaper 10 (i.e., prior to receiving any type of liquid or solid secretion by the wearer) to the wearer's body, or even temporary attachment of a diaper that has been partially loaded. Each of the fastening elements 50 may include a skin-friendly adherent tape, a skin-friendly adhesive dot or patch, or a bead of skin-friendly adhesive, for example, having a regular or irregular shape.

A type of adhesive suitable for the fastening element 50 is commercially available under the name RHODOTAC 315, from Rhodia Ltd. (Manchester, United Kingdom). Other suitable adhesives are described in U.S. Patent Application Publication Nos. 2004/0096489 and 2008/0134418, and U.S. Pat. No. 6,177,482, the respective disclosures of which are hereby expressly incorporated by reference herein in their entirety. A suitable adhesive may be, without limitation, an aqueous acrylate adhesive, an oil-based adhesive, a polyolefin-based adhesive, an acrylate-based pressure sensitive adhesive, a polyurethane-based adhesive, a Kraton-based adhesive, a styrene-butadiene based adhesive formulation, a vinyl acetate-based adhesive formulation, or a silicon-based adhesive. Additionally or alternatively, the skin-friendly adhesive may be free of additives such as tackifiers or biocides, to prevent damage to the skin of the wearer with which diaper 10 comes in contact. Suitable adhesives may have a pH value of about 5 or less, in order to decrease the susceptibility of that adhesive to bacteria, thereby promoting the health of the skin with which diaper 10 comes in contact.

In specific embodiments, the fastening element 50 has a tackiness value in the range of about 0.1 inches to about 2 inches, and in specific embodiments about 0.5 inches, as measured by the Standard Test Method for Tack of Pressure-Sensitive Adhesives by Rolling Ball, ASTM D3121-06, using a 1 mil (25.4 µm) polyester film. Additionally or alternatively, the fastening element 50 may be such that same adheres to the skin with a force in the range between about 0.5N and about 5N, and in specific embodiments between about 0.5N and about 3N, or between about 0.5N and about 2N, and in other specific embodiments between about 0.7N and about 1.5N, with all of these force values being obtained through the test method described in incorporated-by-reference U.S. Patent Application Publication No. 2004/0096489, specifically at FIG. 3 and the description thereof in that publication.

Additionally or alternatively, the fastening element 50 may have a relatively low adhesive strength so as to permit painless detachment from the skin without damage to the skin or hair present on the skin. This relative low strength may for example be in the range between about 0.5N/25 mm and about 3N/25 mm, or between about 0.5N/25 mm and about 2N/25 mm, and more specifically between about 1.0N/25 mm and about 1.5N/25 mm, with all those values being measured by the Standard Test Method for Strength Properties of Tissue Adhesives in T-Peel by Tension Loading, ASTM F2256-05 (2010). In addition, the adhesive defining fastening element 50 may be relative soft, as that property is defined and measured in incorporated-by-reference U.S. Patent Application Publication No. 2008/0134418. In that regard, the degree of softness of the adhesive of fastening element 50 may be less than about 10 mm, as measured by ASTM D937-07 (Standard Test Method for Cone Penetration of Petrolatum) and variations thereof described in that publication.

In the embodiment shown in FIGS. 1-3, the fastening elements 50 are located on the inner face IF of the side panels 35, although this location is intended to be exemplary rather than limiting. For example, the fastening elements 50 may instead be located on the exterior face EF of side panels 35, or on any other portion of the interior or exterior faces IF, EF of diaper 10, including portions forming part of the front portion of diaper 10, such as the side regions 36, or other portions. Further in the illustrated embodiment, each of the side panels 35 includes a single one of the fastening elements 50 with the respective fastening elements 50 being generally equidistant from the longitudinal axis 10y of diaper 10, as seen in FIG. 2.

Figure 5:
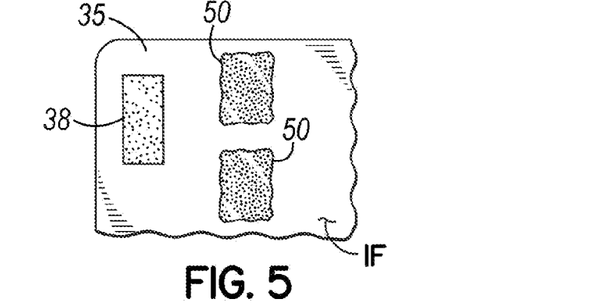
FIG. 5 is a view similar to FIG. 4, showing a side panel in accordance with yet another embodiment of the invention.
Figure 6:
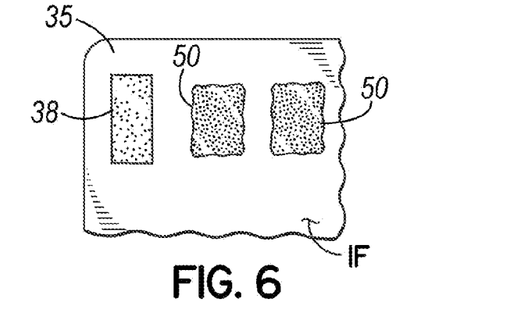
FIG. 6 is a view similar to FIGS. 4 and 5, showing a side panel in accordance with another embodiment of the invention.

A contemplated variation has a pair of fastening elements 50 located at respective distances from the longitudinal axis 10y that are different from one another. Further, contemplated variations include embodiments in which one or more fastening elements 50 are supported on a side panel 35, and in which one or more fastening components 38 are supported directly on a side panel 35 rather than on a tape tab, such as the tape tab 38a of FIGS. 1-3. Embodiments of this type are illustrated at FIGS. 4, 5, and 6. In the embodiment of FIG. 4, the side panel 35 shown in that figure has a single fastening element 50, generally adjacent the fastening component 38. While in that embodiment the fastening element 50 is laterally spaced from the fastening component 38, it is contemplated that fastening element 50 may instead be located immediately adjacent (i.e., in abutting relationship) fastening component 38, or be longitudinally spaced from fastening component 38.

In the embodiments of FIGS. 5 and 6, the side panel 35 shown therein has more than one fastening element 50. More specifically, in the exemplary embodiment of FIG. 5, the side panel 35 has a pair of fastening elements 50 that are spaced from one another in the longitudinal direction of the diaper 10. And in the exemplary embodiment of FIG. 6, the side panel 35 includes a pair of fastening elements 50 that are spaced from one another in the lateral direction of the diaper 10. Yet other variations, not shown herein, are similarly contemplated in which a pair of fastening elements 50 may be spaced from one another in both, the longitudinal and lateral directions of diaper 10.

Figures 7, 8:
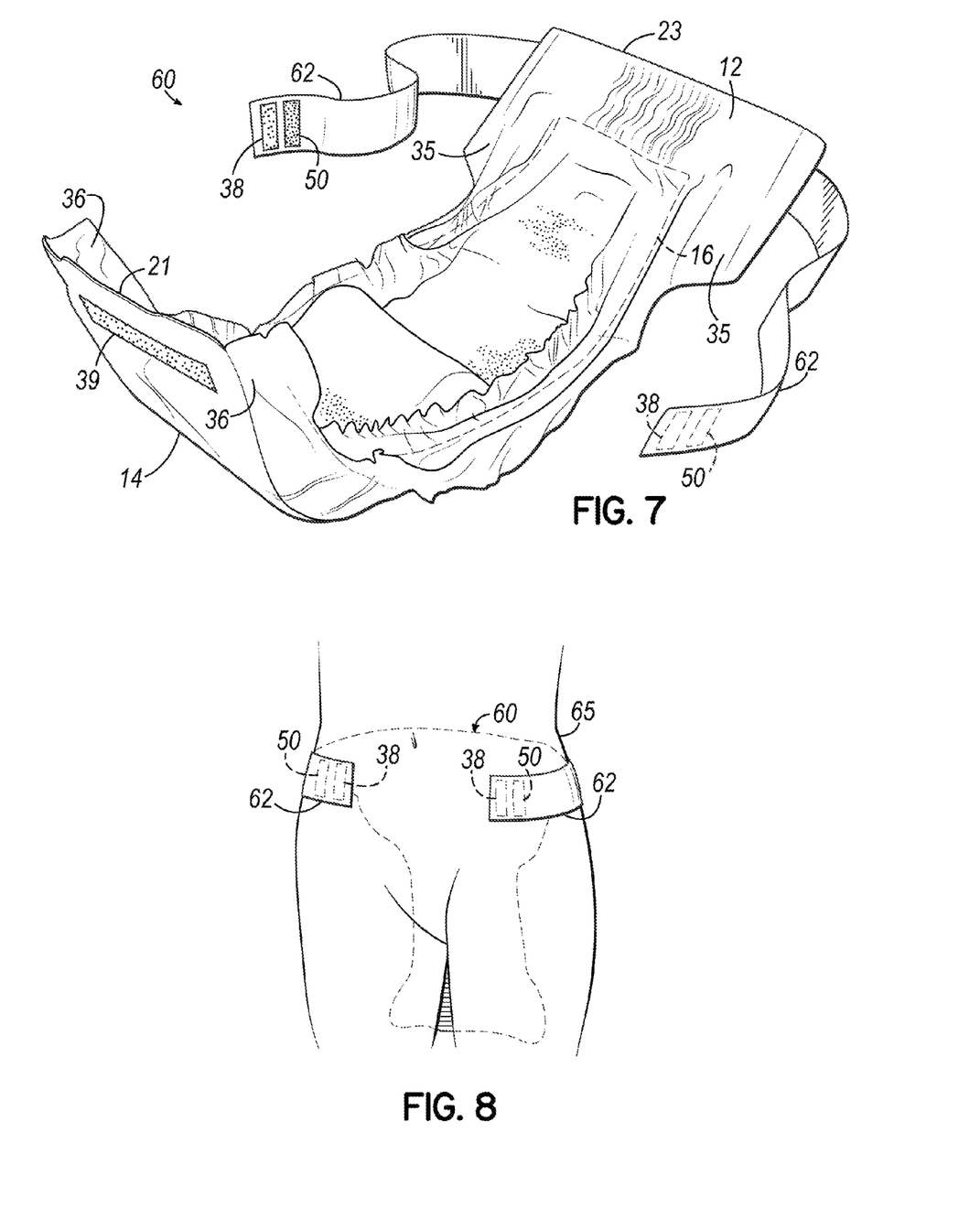
FIG. 7 is a perspective view of a disposable absorbent product in accordance with another embodiment of the invention.
FIG. 8 is a perspective schematic view illustrating an exemplary application of the product of FIG. 7 onto the body of a wearer of that product.

FIG. 7 illustrates another embodiment of a disposable absorbent product in the form of a belted product 60, similar to diaper 10 (FIG. 1), and having a pair of side regions in the form of belt portions 62. For ease of understanding, like reference numerals in FIG. 7 refer to similar features in the preceding figures, the description of which may be referred to for an understanding of the structure and function of those features in FIG. 7 as well. The belted portions 62 are located in the back portion of product 60, and provide a greater fitting range for product 60 around the waist area of the wearer than available, for example, with a diaper such as the diaper 10 of FIG. 1. In the embodiment illustrated in FIG. 7, each of the belted portions 62 has a fastening element 50 similar in type, configuration and contemplated variations, to the fastening element 50 of FIGS. 1-6. In that regard, fastening element 50 permits the product 60 to be temporarily secured against the skin of the wearer, during application of the product 60, through direct adhesive attachment.

FIGS. 8, 9, 10, and 11 describe an exemplary application of product 60 on the body 65 of a wearer. It is understood, notwithstanding, that the illustrated application may also refer to diaper 10 (FIG. 1) around the body 65 of an adult wearer or the body of a child or even a baby. For ease of understanding, like-reference numerals in FIGS. 8-11 refer to similar features in the preceding figures, the description of which may be referred to for an understanding of the structure and function of those features in FIGS. 8-11 as well. FIG. 8 illustrates the product 60 being temporarily secured to the front waist region of the wearer's body 65, via adhesive attachment of the fastening elements 50 against the skin of the wearer. In that regard, the skin-friendly adhesive of fastening elements 50 have sufficient adhesive strength against the skin, so as to support the entire weight of product 60. It is understood that the number and/or position of fastening elements 50 may be different from those of the exemplary fastening elements 50 of product 60. In that regard, a skin-friendly adhesive may be chosen for fastening element(s) 50 that takes that design element into account, so that the one or more fastening elements 50 is/are capable of supporting the entire weight of product 60 when temporarily attached to the skin of the wearer.

Figure 9:
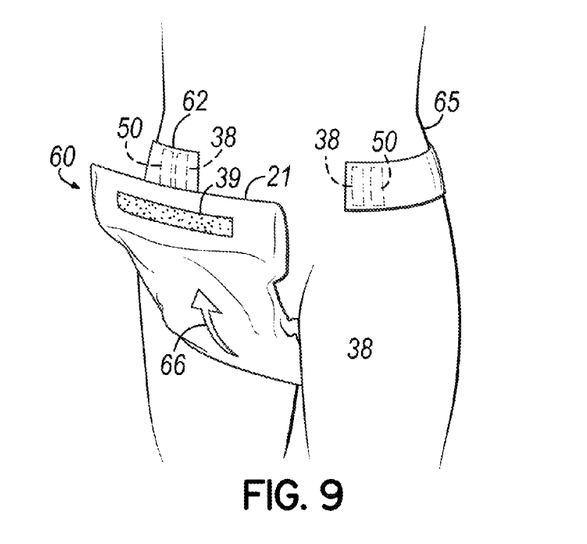
FIG. 9 is a perspective view similar to FIG. 8, illustrating another part of an exemplary application of the product of FIGS. 7 and 8 onto the body of the wearer.
Figure 10:
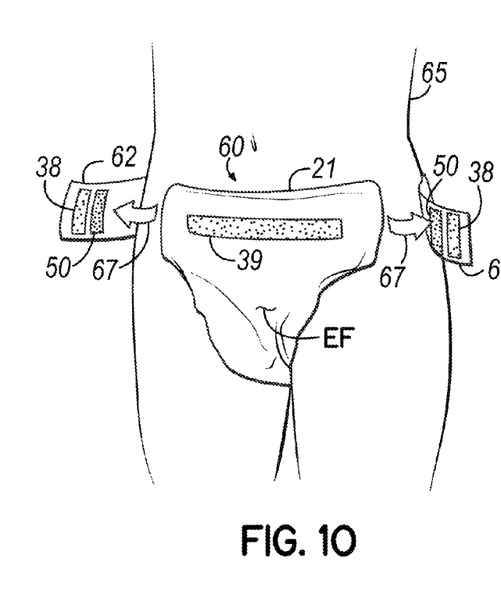
FIG. 10 is a perspective view similar to FIGS. 8 and 9, illustrating yet another part of an exemplary application of the product of FIG. 7-9 onto the body of the wearer.

FIG. 9 illustrates a subsequent step in the exemplary application of product 60 onto the wearer's body 65. While the weight of product 60 is being supported by the adhesive attachment of fastening elements 50 on the skin of body 65, the wearer or a caregiver in charge of the wearer is able to easily move (arrow 66) the front portion of product 60 in between the wearer's legs, toward the front waist region of body 65, without having to manage the back portion of product 60. Once the front portion of product 60 is at the desired position, the wearer or caregiver detaches (arrows 67) the fastening elements 50 from the skin of the wearer, as illustrated at FIG. 10. So as to minimize the discomfort felt by the wearer at the time of detachment of the fastening elements 50, the tackiness of the skin-friendly adhesive of fastening elements 50 may be chosen not to be relative low, as explained above. The application of product 60, as illustrated in FIGS. 8-11 and described herein, can be easily effected by a wearer with limited dexterity. Similarly, in the case of persons with limited mobility, the product 60 can be applied by one, rather than by two or more caregivers.

Figure 11:
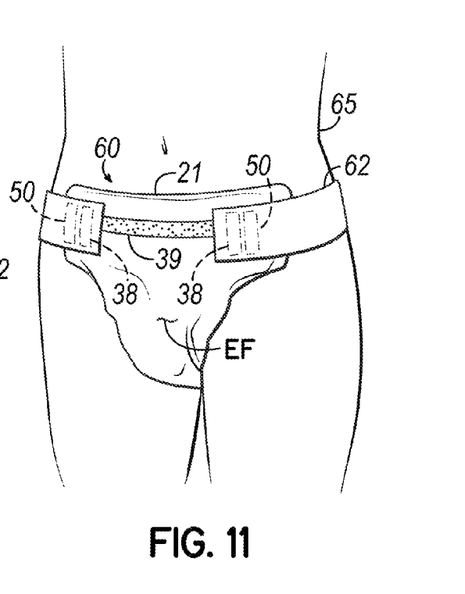
FIG. 11 is a perspective view of the product of FIGS. 7-10, in its fully applied condition on the body of the wearer.

FIG. 11 shows product 60 fully positioned on the body 65 of the wearer. As that figure illustrates, the final position of the fastening elements 50 is such that they are no longer exposed to the skin of the wearer. More specifically, in the fully-applied position of product 60, the fastening elements 50 are not in contact with the skin of the wearer, but rather with the exterior face EF of product 60, in the front portion thereof. In that fully-applied position, the exemplary product 60 is held in place by engagement of a pair of hook-type fastening components 38 with a cooperating fastening feature 39 of product 60, similar to the like-numbered fastening components and fastening features of diaper 10 (FIGS. 1-2).

The exemplary application of product 60 illustrated at FIGS. 8-11 refers to the application of the product on a standing wearer, who may for example be a large-waist patient of a nursing home or some other incontinent person. Those of ordinary skill in the art will readily appreciate that the product 60 may be applied in a similar way onto the body of a person that is lying down, rather than standing, in which case the adhesive strength of fastening elements 50 does not necessarily have to support the entire weight of the product 60, but rather be sufficient to maintain the product 60 temporarily fixed on the body 65 of the wearer during application, while the person is lying down. Further, it is understood that the exemplary application illustrated at FIGS. 8-11 may refer to the application of diaper 10 (FIG. 1) onto the body of a small child or even a baby.

While the exemplary application of FIGS. 8-11 refers to a product 60 in which the fastening elements 50 are positioned so as to engage the front waist portion of body 65, this is not intended to be limiting. Specifically, embodiments are contemplated in which the one or more fastening elements 50 are positioned on product 60 (or any other form of disposable absorbent product) so as to temporarily adhere to the back waist portion, or even to the side portions of body 65, rather than to the front waist portion. In all of those contemplated embodiments, the one or more fastening elements 50 only temporarily adhere to the skin of the wearer, such that, when the disposable absorbent product is fully applied, those fastening elements 50 are no longer in contact with the skin, but rather with other surfaces of the disposable absorbent product.

The temporary nature of the attachment provided by the one or more fastening elements 50 described above obviate the need for skin-friendly adhesives that must adapt to the changing conditions of a wearer's skin during the wearing cycle of the product. Specifically, conventional products that use adhesives for permanent (rather than temporary) attachment to the skin must take into account the effect of sweat and other secretions from the wearer's body during use of the product, which may in some instances cause the product to detach from the skin. By limiting the duration of required adherence of the fastening elements 50 to the skin, the need to address the changing conditions of the skin over time is thus eliminated.

Further, the temporary nature of the attachment to skin of the one or more fastening elements 50 is advantageous in that it limits the length of exposure of the wearer's skin to the skin-friendly adhesive in the fastening element 50. This is desirable in instances in which particular wearers may be particularly sensitive to the materials making up the skin-friendly adhesive. In yet another aspect, the one or more fastening elements 50 advantageously remain available for subsequent applications of the disposable absorbent product onto the body 65 of the wearer. Specifically, the fastening elements 50 can be used after the initial application of the product, should the wearer or caregiver decide to temporarily remove the product from the wearer. For example, the wearer may decide to temporarily remove the product from his/her body to go to the bathroom and subsequently reapply the product onto his/her body. Likewise, a caregiver may decide to temporarily remove the product from the wearer's body to check whether any fluids or solids have been excreted by the wearer, after which the product is reapplied on the wearer's body.

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A disposable absorbent product extending longitudinally along a longitudinal axis and laterally along a transverse axis, with the transverse axis conceptually dividing the product into first and second hemispheres, the product comprising:
   a topsheet;
   a backsheet overlaying said topsheet;
   an absorbent core disposed between said topsheet and said backsheet for storing fluid secreted by the wearer of the disposable absorbent product;
   a pair of side regions extending laterally outboard of said absorbent core, each of said side regions having a first face configured to face the wearer during use and a second face opposite said first face;

at least one skin-friendly adhesive element in the first hemisphere in at least one of said side regions for temporarily attaching the disposable absorbent product to the skin of the wearer; and
a fastening component in the first or second hemisphere, configured for securing the first and second hemispheres to one another on the wearer,
wherein said at least one skin-friendly adhesive element is in contact with the second hemisphere when the first and second hemispheres are secured to one another on the wearer.

2. The disposable absorbent product of claim 1, wherein said fastening component includes the hook or loop member of a hook-and-loop fastener.

3. The disposable absorbent product of claim 1, wherein said fastening component is located on said first face of one of said side regions.

4. The disposable absorbent product of claim 1, wherein said fastening component includes a tab extending outwardly from one of said side regions.

5. The disposable absorbent product of claim 1, wherein said at least one skin-friendly adhesive element includes first and second skin-friendly adhesive elements located on respective ones of said pair of side regions.

6. The disposable absorbent product of claim 5, wherein said first and second skin-friendly adhesive elements are substantially equidistant from the longitudinal axis of the product.

7. The disposable absorbent product of claim 1, wherein said at least one skin-friendly adhesive element includes first and second spaced apart skin-friendly adhesive elements located on one of said side regions.

8. The disposable absorbent product of claim 7, wherein said first and second skin-friendly adhesive elements are longitudinally spaced from one another.

9. The disposable absorbent product of claim 1, wherein said at least one skin-friendly adhesive element is located on said first face of one of said side regions.

10. The disposable absorbent product of claim 1, wherein said at least one skin-friendly adhesive element has a tackiness value in the range of about 0.1 inches to about 2 inches.

11. The disposable absorbent product of claim 1, wherein said at least one skin-friendly adhesive element has an adhesive strength, when adhered to skin, in the range from about 0.5N to about 5N, as measured by the Standard Test Method for Tack of Pressure-Sensitive Adhesives by Rolling Ball using a 1 mil polyester film.

12. The disposable absorbent product of claim 1, wherein said at least one skin-friendly adhesive element is free from tackifiers and biocides.

13. The disposable absorbent product of claim 1, wherein said at least one skin-friendly adhesive element is made up of an adhesive having a pH value of about 5 or less.

14. The disposable absorbent product of claim 1, wherein said at least one skin-friendly adhesive element is made up of an adhesive having a softness less than about 10 mm.

15. The disposable absorbent product of claim 1, wherein said side regions define respective belt portions of the product configured to wrap around the body of the wearer.

16. The disposable absorbent product of claim 1, wherein the product has a front portion configured to face the front part of the wearer's body, a back portion configured to face the back part of the wearer's body, and a crotch portion between said front and back portions, said back portion being located in the first hemisphere of the product.

17. A disposable absorbent diaper extending longitudinally along a longitudinal axis and laterally along a transverse axis, the diaper further having a front portion configured to face the front of the wearer's body during use and a back portion configured to face the back of the wearer's body during use, the product comprising:
a permeable topsheet;
an impermeable backsheet overlaying said topsheet;
an absorbent core disposed between said topsheet and said backsheet for storing fluid secreted by the wearer of the diaper;
a pair of side panels in said back portion and extending laterally outboard of said absorbent core, each of said side panels having a first face configured to face the wearer during use and a second face opposite said first face;
a skin-friendly adhesive element in the back portion, on said first face of each of said side panels, for temporarily attaching the diaper to the skin of the wearer; and
at least one hook-and-loop fastener member in the back portion configured for securing the front and back portions to one another on the wearer,
wherein said skin-friendly adhesive element on said first face of each of said side panels is in contact with the front portion when the front and back portions are secured to one another by said at least one hook-and-loop fastener member.

18. The diaper of claim 17, wherein said at least one hook-and-loop fastener member includes first and second hook-and-loop fastener members located on said side panels.

19. The diaper of claim 17, wherein said at least one hook-and-loop fastener member is a hook fastener configured for direct entangled engagement with said backsheet in the front portion.

20. The diaper of claim 17, further comprising at least one loop fastener member in the front portion, said at least one hook-and-loop fastener member being a hook fastener configured for entangled engagement with said at least one loop fastener member in the front portion.

21. A belted disposable absorbent product extending longitudinally along a longitudinal axis and laterally along a transverse axis, the product having a front portion configured to face the front of the wearer's body during use and a back portion configured to face the back of the wearer's body during use, the product comprising:
a permeable topsheet;
an impermeable backsheet overlaying said topsheet;
an absorbent core disposed between said topsheet and said backsheet for storing fluid secreted by the wearer of the disposable absorbent product;
a pair of belt portions in the back portion of the product and extending laterally outboard of said absorbent core, each of said belt portions having a first face configured to face the wearer during use and a second face opposite said first face;
a skin-friendly adhesive element in each of said belt portions, for temporarily attaching the disposable absorbent product to the skin of the wearer; and
a pair of hook-and-loop fastener members in the back portion, and configured for securing the front and back portions of the product to one another on the wearer,
wherein each said skin-friendly adhesive element is in contact with the front portion of the product when the front and back portions are secured to one another by said hook-and-loop fastener members.

22. The belted product of claim 21, wherein said hook-and-loop fastener members are located on said belt portions.

23. The belted product of claim 21, wherein said skin-friendly adhesive elements are located on respective first faces of said belt portions.

24. The belted product of claim 21, wherein said hook-and-loop fastener members are hook fasteners configured for direct entangled engagement with said backsheet in the front portion.

25. The belted product of claim 21, wherein said skin-friendly adhesive elements and said hook-and-loop fastener members are located on said first faces of said belt portions.

26. The belted product of claim 21, further comprising at least one loop fastener member in the front portion, at least one of said hook-and-loop fastener members being a hook fastener configured for entangled engagement with said at least one loop fastener member in the front portion.

\* \* \* \* \*